United States Patent [19]
Lee

[11] Patent Number: 5,967,412
[45] Date of Patent: Oct. 19, 1999

[54] AIR FRESHENER DISPENSER

[76] Inventor: Song Won Lee, 3201 Henderson Mill Rd., Apt.9D, Chamblee, Ga. 30341

[21] Appl. No.: 08/995,581

[22] Filed: Dec. 22, 1997

[51] Int. Cl.[6] ..................................................... A24F 25/00
[52] U.S. Cl. .............................................. 239/57; 239/60
[58] Field of Search ................................ 239/34, 53–59, 239/274, 60

[56] References Cited

U.S. PATENT DOCUMENTS

| | | | |
|---|---|---|---|
| 2,534,464 | 12/1950 | Marini et al. | 299/82.5 |
| 3,033,471 | 5/1962 | Horn | 239/274 |
| 3,390,817 | 7/1968 | Heropoulos | 222/180 |
| 3,617,214 | 11/1971 | Dolac | 21/77 |
| 4,523,870 | 6/1985 | Spector | 239/59 |
| 4,570,824 | 2/1986 | Bolling | 222/39 |
| 4,615,486 | 10/1986 | Konicek | 239/274 |
| 4,619,383 | 10/1986 | Konicek | 222/556 |
| 4,632,310 | 12/1986 | Konicek | 239/43 |
| 4,712,737 | 12/1987 | Hecking | 239/58 |
| 4,931,258 | 6/1990 | Zlotnik et al. | 239/55 |
| 5,148,984 | 9/1992 | Bryson, Jr. et al. | 239/55 |
| 5,390,833 | 2/1995 | Baumann | 222/505 |
| 5,598,954 | 2/1997 | Salzano | 222/162 |

FOREIGN PATENT DOCUMENTS

| | | | |
|---|---|---|---|
| 2640163 | 6/1990 | France | 239/274 |

*Primary Examiner*—Kevin P. Shaver
*Assistant Examiner*—Dinh Q. Nguyen
*Attorney, Agent, or Firm*—Bernstein & Associates P.C.

[57] ABSTRACT

A dispensing device (7) that is intended to be mounted on a vertical planar surface such as a door (10). The dispensing device (7) includes an enclosure (13) having a first opening (34) and a second opening (37) defined therein. The first opening (34) contains a first airflow valve (43) and the second opening contains a second airflow valve (46). An odorous substance (40) is disposed inside the enclosure (13) between the two airflow valves (43,46). When the door (10) swings open or closed, airflow generated along the surface of the door (10) passes through the airflow valves (43,46) to release the odors from the odorous substance (40) into the area surrounding the door (10).

25 Claims, 3 Drawing Sheets

5,967,412

AIR FRESHENER DISPENSER

FIELD OF THE INVENTION

The present invention relates to air freshener dispensers, and more particularly to a door-mounted dispenser that is capable of dispensing a fragrance in response to the motion and airflow generated by opening or closing a door.

BACKGROUND OF THE INVENTION

Devices for dispensing air fresheners or fragrances in a local area surrounding the device are well known and usually are divided into passive and active devices. Some of the more prevalent passive air freshening devices include solid fragrant materials that are enclosed in a housing having apertures. The solid slowly releases a volatilized fragrance over a long period of time until the fragrance is spent. The housing associated with this type of dispensing device is usually constructed of a lightweight plastic and is provided with a self-adhesive strip for attaching the dispensing device to planar surfaces. In many cases, when the fragrance is spent, the entire unit is discarded. Other devices include replaceable cartridges or blocks, of dispensing devices, for periodic recharging of the device. Due to their small size and ability to attach to any planar surface, these devices can be placed in numerous locations with little or no intrusion into the surrounding area. Other passive air fresheners, especially those used in restrooms, do not have any enclosure and are simply comprised of a block of chemical that slowly releases a fragrance. An example of this type of dispensing device is a solid block that is placed in the clean water reservoir for a standard toilet.

An example of the active type of air freshening device is the aerosol spray type where the fragrance is stored under pressure in gaseous form. While these spray cans provide a powerful charge of dispensing device to a local area, there are several disadvantages to their use including safety, especially for children, and environmental concerns.

It has been known in the prior art to combine active and passive air freshening by mounting a dispensing device to a door. An example of a door-activated dispensing device is disclosed in U.S. Pat. No. 4,619,383 issued to Konicek. Konicek discloses a dispensing device that includes a reservoir for holding a fragrant liquid. The reservoir is positioned over a pad that absorbs the liquid and provides for release of the fragrance into the room. The reservoir provides liquid to the pad through the action of a pivoting valve that is normally closed but opens for a brief period of time when the door is moved. The pivoting valve is fulcrumed such that it swings from one closed position through the open position to another closed position in response to the motion of the door. While the device takes advantage of the motion of the door to provide active and passive air freshening, its main drawback is that it requires the user to store and handle liquid chemicals for refilling the unit.

What is needed is a disposable dispensing device that combines active and passive air freshening from a solid fragrant or odorous substance by taking advantage of the airflow and the motion generated by the opening of a door.

SUMMARY OF THE INVENTION

Generally described, the present invention provides an air freshening device that combines active and passive air freshening by relying on a door-activated dispensing device.

In a preferred embodiment, the present invention provides an enclosure capable of being mounted to a vertical planar surface such as the surface of a door and having a first opening and a second opening. A first airflow valve is disposed inside the first opening and a second airflow valve is disposed inside the second opening. The valves allow the air that flows along the surface of the door in response to the motion of the door to pass through the enclosure. The air passing through the enclosure volatilizes an odorous substance that is disposed inside the enclosure and carries the odor out of the enclosure into the room. The airflow valves are normally closed but are not sealed so that continuous passive air freshening occurs as the odors from the odorous substance are constantly flowing into the room. Active air freshening occurs when a charge of the odor is delivered into the room in response to the motion of the door.

It is an object of the present invention to provide a dispensing device that mounts to a vertical planar surface such as the side of a door.

It is another object to provide a dispensing device that combines active and passive air freshening.

Another object is to provide an air freshening device that is constructed of lightweight, inexpensive materials that are disposable.

A further object is to provide an enclosure having a first airflow valve and a second airflow valve that control the flow of air through a first opening and a second opening in the enclosure.

An additional object of the present invention is to provide an air freshening device that detachably mounts to a vertical planar surface by means of a self-adhesive strip.

Other objects, features, and advantages of the present invention will become apparent upon reading the following detailed description of embodiments of the invention, when taken in conjunction with the accompanying drawings and the appended claims.

BRIEF DESCRIPTION OF THE DRAWINGS

The invention is illustrated in the drawings in which like reference characters designate the same or similar parts throughout the figures of which.

DESCRIPTION OF THE PREFERRED EMBODIMENTS

Figure 1:
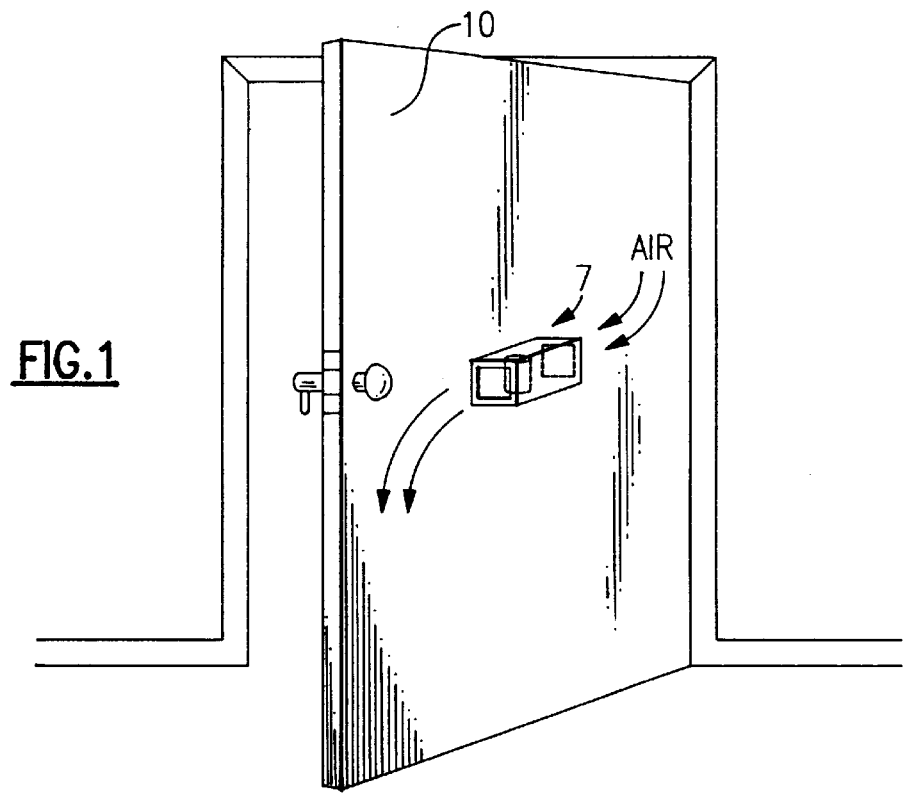
FIG. 1 is a perspective view of the present invention mounted to a door.
Figure 2:
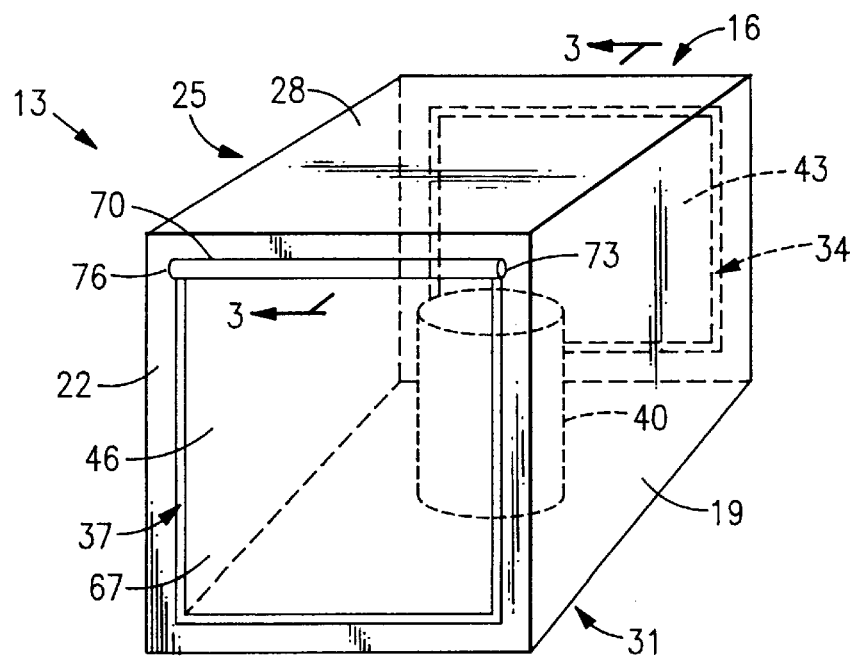
FIG. 2 is a perspective view of the enclosure of the present invention.

Referring to FIGS. 1–5B generally, and initially referring to FIG. 1, the air freshener dispensing device 7 of the present invention is shown mounted to a standard door 10. Referring to FIG. 2, the air freshener dispensing device 7 has an enclosure 13. The enclosure 13 is preferably constructed of a lightweight material such as paper, cardboard, plastic, metal or the like. The preferred materials are lightweight and relatively inexpensive in order to allow for economically feasible disposal of the product within a relatively short time period. The enclosure 13 is preferably constructed of a six-sided shape where each side is a rectangle. Other shapes would be equally functional, however, the six-sided shape with straight edges and flat sides is preferred because it is easier to manufacture than shapes with curved sides. Accordingly, the enclosure 13 has four side walls 16, 19, 22, and 25; a top wall 28; and, a bottom wall 31. Side wall 16 has a first opening 34 defined therein. When the door 10 is opened, the motion generates airflow into the enclosure 13 through the first opening 34 and out of the enclosure 13 through a second opening 37. The first opening 34 is preferably rectangular shaped and disposed substantially perpendicular to the door 10. The second opening 37 can be positioned on any of the other walls except for the back wall 25. However, the preferred position for the second opening is on side wall 22 which is located opposite from the first opening 34.

An odorous substance 40 is preferably positioned inside the enclosure between the first opening 34 and the second opening 37. The odorous substance 40 preferably comprises a solid chemical that slowly releases an odor or fragrance. The substance 40 could also include an odorous gel, liquid, gas or any type of odor emitting substance known to those skilled in the art. Odorous substances like substance 40 are widely available from many commercial sources and can be purchased as an "off the shelf" item without any special manufacturing required. When the door 10 moves, it causes a charge of odor from the odorous substance 40 to be forced out of the enclosure 13 into the surrounding area.

In order to prevent the odorous substance 40 from being constantly exposed to air flow and therefore being spent too fast, a first airflow valve 43 and a second airflow valve 46 are disposed inside the first opening 34 and the second opening 37.

Figure 3:
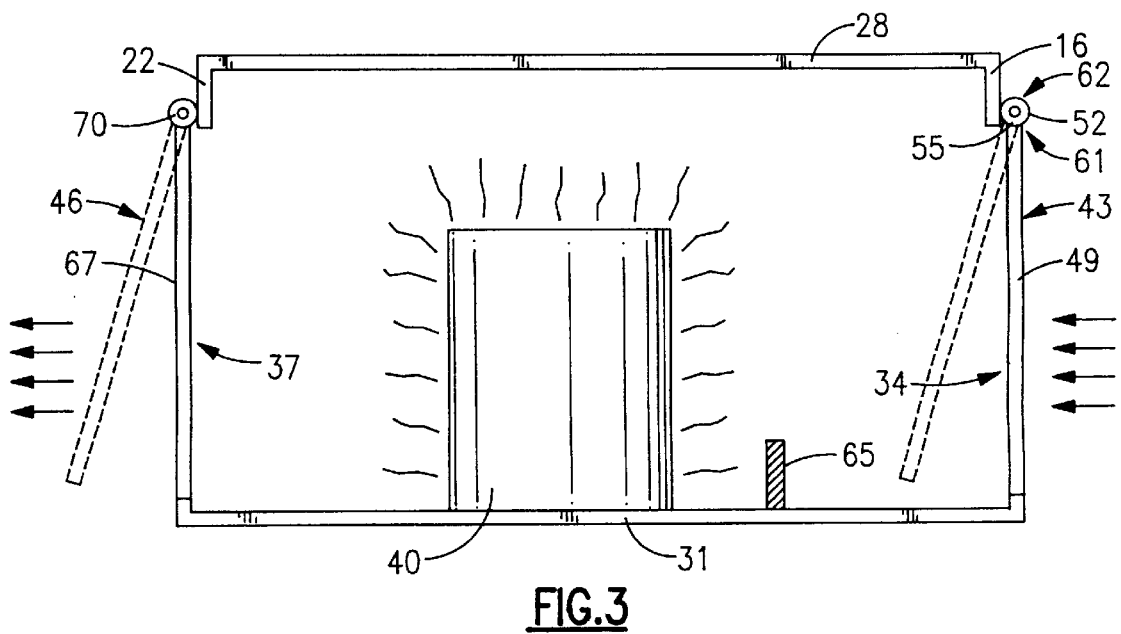
FIG. 3 is a sectional side elevation view of the enclosure of the present invention taken along line 3—3.

As best shown in FIG. 3, the first valve 43 is preferably equipped with a gate 49 that is hingedly attached to a pin 52. The gate 49 is preferably constructed of a very thin gauge of paper, cardboard, metal, plastic or the like, that is thinner than the remainder of the enclosure 13 and is capable of being moved by the forces and the amount of airflow generated by the motion of the door 10. The pin 52 rotates inside a set of bearings 55 and 58 (shown in FIG. 5A) that are disposed adjacent to the top 61 of the opening 34. The bearings 55 and 58 may be integrally formed in the enclosure 13 or attached to the outside of the enclosure by mechanical fasteners, glue, or the like (not shown) as is known to those skilled in the art. The bearings 55 and 58 are preferably formed with narrow openings 62 and 64 (not shown) at the top for frictionally fitting the pin 52 into the bearings 55 and 58 so that the pin 52 remains seated while the gate 49 rotates. When the air flows through the enclosure 13, the gate 49 rotates into the enclosure 13 through the first opening 34. In order to prevent the gate 49 from rotating too far into the enclosure and coming into contact with the odorous substance 40, a stop 65 projects from the inside of the enclosure 13 and limits the travel of the gate 49.

The second airflow valve 46 operates in substantially the same manner as the first airflow valve 43 except its gate 67 rotates on a pin 70 which is seated in a set of bearings 73 and 76 (shown in FIG. 2). Due to the direction of the airflow generated by the door 10, the gate 67 rotates out of the opening 37 away from the enclosure 13.

The valves 43 and 46 are normally closed and substantially cover the openings 34 and 37, but the valves preferably do not form an airtight seal. An airtight seal is not required because a certain amount of passive air freshening is desirable at the times when the door is still.

Figure 4:
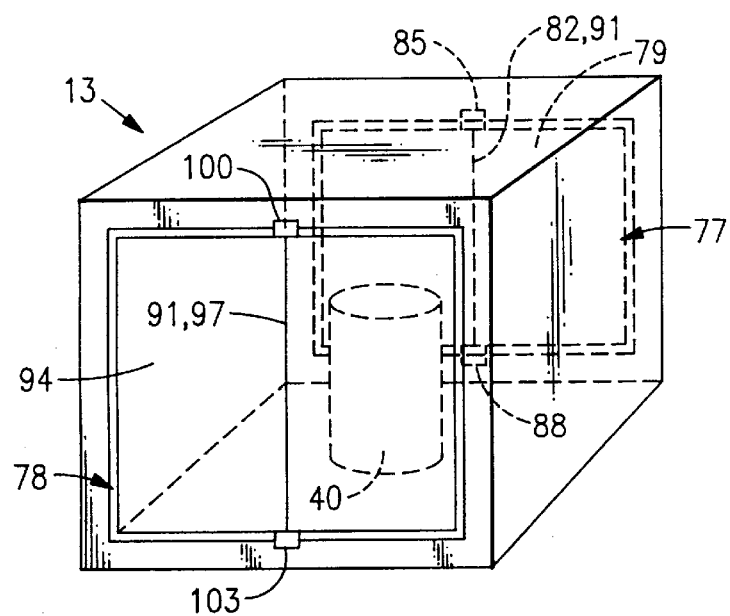
FIG. 4 is a perspective view of an alternate embodiment of the present invention.

Turning to FIG. 4, an alternate embodiment of the present invention comprises a similarly shaped enclosure 13 but includes a different set of airflow valves 77 and 78. The first airflow valve 77 includes a gate 79 that attaches to a vertically mounted pintle 82. The pintle 82 is attached to the gate 79 at approximately the midpoint of the gate 79. The pintle 82 rotates in a set of bearings 85 and 88. The bearings 85 and 88 are preferably disposed adjacent to the openings 34 and 37 and integrally formed in the enclosure, but the bearings 85 and 88 may be attached to the enclosure by mechanical fasteners, glue, or the like (not shown) as is known to those skilled in the art. With the gate 79 attached to a pintle 82, the airflow causes the normally closed gate 79 to spin around a vertical axis 91 to open the valve. The gate 79 is also normally closed to prevent the odorous substance 40 from becoming spent too fast from too much exposure to ambient air. However, the gate 79 and the enclosure 13 preferably do not form an airtight seal so that passive air freshening can occur when the door 10 is still.

The second airflow valve 78 operates in substantially the same manner as the first airflow valve 77 except its gate 94 rotates on a vertically mounted pintle 97 which is seated in a set of bearings 100 and 103. Although the vertically oriented pintles 82 and 97 are preferable, the axis of rotation is not critical and therefore many different axial configurations for the gates 79 and 94 would also work.

Figure 5A:
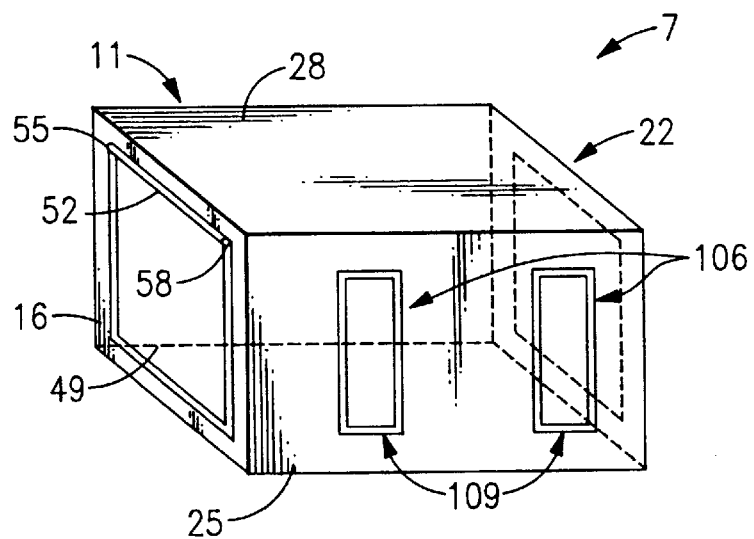
FIG. 5A is a perspective view of the back wall of the enclosure equipped with pressure sensitive strips for mounting; and, FIG. 5B is an exploded perspective view of a mounting bracket attached to the door and a mounting plate attached to the back wall of the enclosure.
Figure 5B:
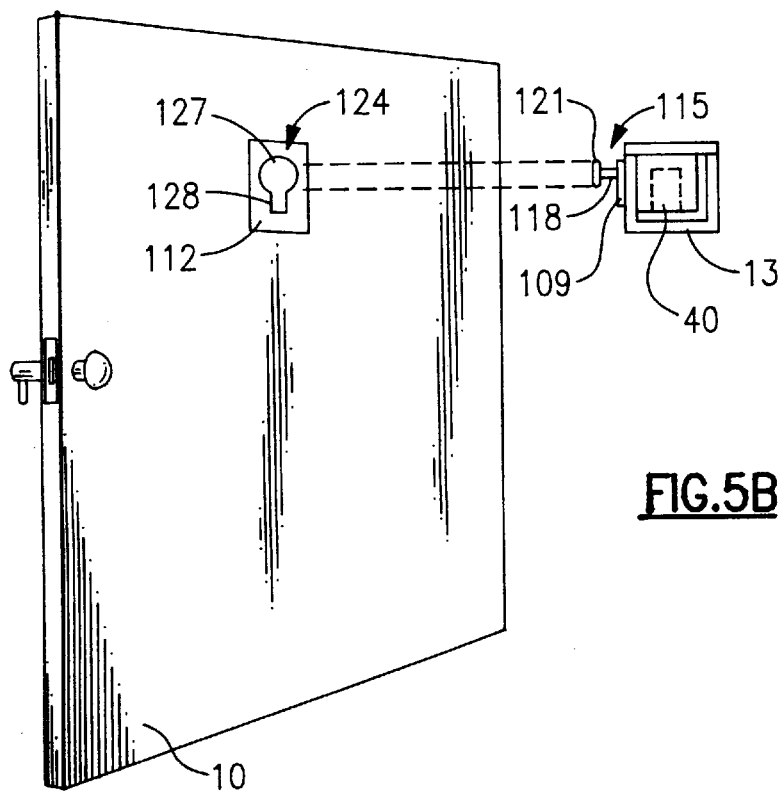

Turning to FIGS. 5A and 5B, several options are shown for mounting the device 7 to a planar surface. In FIG. 5A, a set of pressure sensitive adhesive strips 106 is shown. The adhesive strips 106 are preferably fixedly attached to the back wall 25. The adhesive strips 106 are well known in the art and widely available from numerous sources. In order to install the strips 106 a backing strip 109 is removed and the device 7 is pressed against the vertical planar surface. The adhesive strips 106 are preferably manufactured with an adhesive strong enough to hold the device 7 but not too strong to make removal for disposal purposes too difficult.

As an alternative shown in FIG. 5B, the enclosure 13 can be equipped with a mounting plate 109 for connection to a mounting bracket 112 that attaches to the door 10. The mounting plate 109 is a flat plate having a projection 115 that preferably includes a short shaft 118 with a circular disc 121 attached thereto. The mounting plate 109 is preferably constructed of metal or hard plastic and can be attached to the enclosure 13 with mechanical fasteners, adhesives, or the like as is known to those skilled in the art.

The bracket 112 has a slot 124 that has a wider section 127 at one end and a narrower section 128 at the other end which enables the projecting part 115 on the mounting plate 109 to be detachably inserted into the mounting bracket 112. The bracket 112 is preferably attached to the door with mechanical fasteners, glue, or the like as is known to those skilled in the art.

The circular disc 121 fits into the top of the slot 124 and is captured by the narrower portion 128 of the slot 124 when the shaft 118 slides down the slot 124. In this manner the mounting plate 109 is held securely in the slot 124 on the mounting bracket 112, but the mounting plate 109 can be easily removed from the bracket 112 by sliding the shaft 118 upward in the slot 124 until the circular disc 121 can be removed from the wider section 127 of the slot 124. Accordingly, the male/female quick connect attachment of the mounting plate 109 to the mounting bracket 112 facilitates quick and easy disposal of the entire device 7 when the odorous substance 40 is spent.

Accordingly, an advantage of the present invention is that the device 7 is easily detachable from the planar surface for disposal which eliminates the need for storage and handling of potentially harmful substances by the end user.

Another advantage of the present invention is that the device 7 provides both passive and active air freshening.

Yet an additional advantage of the present invention is that it can be constructed of lightweight, inexpensive materials and is easy to manufacture. Accordingly, it is feasible to produce the invention as a disposable product if so desired.

While the invention has been described in connection with certain preferred embodiments, it is not intended to limit the scope of the invention to the particular forms set forth, but, on the contrary, it is intended to cover such alternatives, modifications, and equivalents as may be included within the spirit and scope of the invention as defined by the appended claims.

I claim:

1. A dispensing device capable of mounting to a planar surface, the dispensing device, comprising:
    a) an enclosure having a first opening and a second opening defined therein;
    b) a first airflow valve movably attached to the enclosure and disposed inside the first opening such that the first airflow valve is movable in response to airflow therethrough.
    c) a second airflow valve associated with the enclosure and disposed inside the second opening;
    d) means for containing an odorous substance;
    e) means for mounting the enclosure to the planar surface.

2. The apparatus of claim 1, wherein the first opening is capable of being oriented substantially perpendicular to the planar surface.

3. The apparatus of claim 1, wherein the first airflow valve is pivotally attached to the enclosure.

4. A dispensing device capable of mounting to a planar surface, comprising:
    a) an enclosure having a first opening and a second opening defined therein;
    b) a first airflow valve pivotally attached to the enclosure and disposed inside the first opening;
    c) a second airflow valve associated with the enclosure and disposed inside the second opening;
    d) means for containing an odorous substance; and
    e) means for mounting the enclosure to the planar surface.

5. The apparatus of claim 4, wherein the first airflow valve further comprises:
    a) a first bearing disposed on the enclosure adjacent to the first opening;
    b) a second bearing disposed on the enclosure adjacent to the first opening opposite from the first bearing;
    c) a pin capable of being supported by the first and second bearing and capable of rotating therein; and,
    d) a gate attached to the pin and capable of rotating relative to the enclosure.

6. The apparatus of claim 5, further comprising:
    a) a stop projecting from the inside surface of the enclosure and capable of limiting the travel of the gate.

7. The apparatus of claim 4, wherein the first airflow valve comprises:
    a) a first bearing disposed on the enclosure adjacent to the first opening;
    b) a second bearing disposed on the enclosure adjacent to the first opening opposite from the first bearing;
    c) a pintle extending across the first opening from the first bearing to the second bearing; and,
    d) a gate having a midpoint substantially equidistant from a first edge and a second edge of the gate, the gate attached to the pintle at its midpoint and capable of rotating inside the first opening.

8. The apparatus of claim 4, wherein the mounting means comprises a pressure sensitive strip attached to the enclosure and capable of fixedly mounting on the planar surface.

9. The apparatus of claim 4, wherein the mounting means comprises
    a) a mounting bracket fixedly attached to the planar surface; and,
    b) a mounting plate fixedly attached to the enclosure and capable of detachably engaging with the support bracket.

10. The apparatus of claim 4, wherein the enclosure further comprises:
    a) at least two opposed side walls;
    b) a top wall attached to the side walls;
    c) a bottom wall attached to the side walls; and,
    d) a back wall attached to the side walls.

11. The apparatus of claim 10 wherein the side walls and back wall are quadrilateral.

12. The apparatus of claim 4, further comprising an odorous substance disposed inside the containing means.

13. The apparatus of claim 12 wherein the odorous substance exists in a state selected from the group consisting of solid, liquid, and gas.

14. The apparatus of claim 4 wherein the first opening is capable of being oriented substantially perpendicular to the planar surface.

15. A dispensing device capable of mounting to a planar surface, comprising:
    a) an enclosure having at least four quadrilateral side walls, a quadrilateral top wall and a quadrilateral bottom wall, one of the at least four side walls having a first opening defined therein, the first opening disposed substantially perpendicular to the vertical planar surface, the enclosure having a second opening defined therein, the second opening disposed on the sidewall opposite from the first opening;
    b) a first airflow valve pivotally attached to the enclosure and disposed inside the first opening;
    c) a second airflow valve attached to the enclosure and disposed inside the second opening;
    d) means for containing an odorous substance; and,
    e) means for mounting the enclosure to the planar surface.

16. The apparatus of claim 15, wherein the first airflow valve further comprises:
    a) a first bearing disposed on the enclosure adjacent to the first opening;
    b) a second bearing disposed on the enclosure adjacent to the first opening opposite from the first bearing;
    c) a pin capable of being supported by the first and second bearing and capable of rotating therein; and,
    d) a gate attached to the pin and capable of rotating relative to the enclosure.

17. The apparatus of claim 15, further comprising:
    a) a stop projecting from the inside surface of the enclosure and capable of limiting the travel of the gate.

18. The apparatus of claim 15, wherein the first airflow valve comprises:
    a) a first bearing disposed in the enclosure adjacent to the first opening;

b) a second bearing disposed in the enclosure adjacent to the first opening opposite from the first bearing;

c) a pintle extending across the first opening from the first bearing to the second bearing; and, d) a gate having a midpoint substantially equidistant from a first edge and a second edge of the gate, the gate attached to the pintle at its midpoint and capable of rotating inside the first opening.

19. The apparatus of claim 15, further comprising an odorous substance disposed inside the containing means.

20. The apparatus of claim 19, wherein the odorous substance exists in a state selected from the group consisting of solid, liquid, and gas.

21. A dispensing device capable of mounting to a planar surface, the dispensing device, comprising:

a) an enclosure having at least four quadrilateral side walls, a quadrilateral top wall and a quadrilateral bottom wall, one of the at least four side walls having a first opening defined therein, the first opening disposed substantially perpendicular to the planar surface, the enclosure having a second opening defined therein, the second opening located in the side wall opposite from the first opening;

b) a first airflow valve attached to the enclosure and disposed inside the first opening, the first airflow valve having a first bearing disposed on the enclosure adjacent to the first opening, a second bearing disposed on the enclosure adjacent to the first opening opposite the first bearing, a pin capable of being supported by the first and second bearing and capable of rotating relative to the first and second bearing, and a gate attached to the pin and capable of rotating relative to the enclosure;

c) a second airflow valve attached to the enclosure and disposed inside the second opening;

d) means for containing an odorous substance inside the enclosure; and, e) means for mounting the enclosure to the planar surface.

22. A dispensing device capable of mounting to a planar surface comprising:

a) an enclosure having a first opening and a second opening defined therein;

b) a first airflow valve pivotally attached to the enclosure such that when in a closed position the first valve substantially blocks the first opening and when pivoted in response to air movement passing through the enclosure the first valve permits passage of air through the first opening;

c) a second airflow valve pivotally attached to the enclosure such that when in a closed position the second valve substantially blocks the second opening and when pivoted in response to air movement passing through the enclosure the second valve permits passage of air through the second opening;

d) means for containing an odorous substance; and e) means for mounting the enclosure to the planar surface.

23. The apparatus of claim 22, wherein the first opening is capable of being oriented substantially perpendicular to the planar surface.

24. A dispensing device capable of mounting to a planar surface, comprising:

a) an enclosure having a first opening and a second opening defined therein;

b) a first airflow valve pivotally attached to the enclosure and disposed inside the first opening;

c) means for containing an odorous substance; and d) means for mounting the enclosure to the planar surface.

25. The apparatus of claim 24, wherein the first opening is capable of being oriented substantially perpendicular to the planar surface.

* * * * *